(12) United States Patent
Hataoka

(10) Patent No.: US 8,871,457 B2
(45) Date of Patent: *Oct. 28, 2014

(54) METHOD FOR IMMOBILIZING GLUCOSE OXIDASE ON A SELF-ASSEMBLED MONOLAYER

(71) Applicant: Panasonic Corporation, Kadoma (JP)

(72) Inventor: Yukari Hataoka, Osaka (JP)

(73) Assignee: Panasonic Healthcare Co., Ltd, Ehime (JP)

( * ) Notice: Subject to any disclaimer, the term of this patent is extended or adjusted under 35 U.S.C. 154(b) by 155 days.

This patent is subject to a terminal disclaimer.

(21) Appl. No.: 13/627,811

(22) Filed: Sep. 26, 2012

(65) Prior Publication Data

US 2013/0029364 A1    Jan. 31, 2013

Related U.S. Application Data

(63) Continuation of application No. PCT/JP2011/004127, filed on Jul. 21, 2011.

(30) Foreign Application Priority Data

Oct. 19, 2010   (JP) ................. 2010-234314

(51) Int. Cl.
| | | |
|---|---|---|
| C12N 11/02 | (2006.01) | |
| C12Q 1/54 | (2006.01) | |
| G01N 33/553 | (2006.01) | |
| G01N 33/543 | (2006.01) | |
| C12N 9/04 | (2006.01) | |
| G01N 27/327 | (2006.01) | |
| C12Q 1/26 | (2006.01) | |

(52) U.S. Cl.
CPC .............. *C12Q 1/26* (2013.01); *G01N 2610/00* (2013.01); *G01N 33/553* (2013.01); *G01N 33/54353* (2013.01); *C12N 9/0006* (2013.01); *G01N 27/3272* (2013.01); *C12N 11/02* (2013.01); *G01N 27/3275* (2013.01)
USPC ........................................... 435/14; 435/177

(58) Field of Classification Search
CPC ....... C12N 11/12; C12Q 1/26; G01N 2610/00
USPC .................................................. 435/14, 177
See application file for complete search history.

(56) References Cited

U.S. PATENT DOCUMENTS

| | | |
|---|---|---|
| 5,137,804 A | 8/1992 | Greene et al. |
| 5,391,478 A | 2/1995 | Greene et al. |
| 5,969,758 A | 10/1999 | Sauer et al. |
| 6,037,577 A | 3/2000 | Tanaka et al. |
| 6,061,093 A | 5/2000 | Yonemoto |
| 6,115,066 A | 9/2000 | Gowda et al. |
| 6,235,535 B1 | 5/2001 | Keinanen et al. |
| 6,344,877 B1 | 2/2002 | Gowda et al. |
| 6,366,321 B1 | 4/2002 | Yonemoto |
| 6,406,921 B1 | 6/2002 | Wagner et al. |
| 6,475,808 B1 | 11/2002 | Wagner et al. |
| 6,576,478 B1 | 6/2003 | Wagner et al. |
| 6,582,969 B1 | 6/2003 | Wagner et al. |
| 6,596,545 B1 | 7/2003 | Wagner et al. |
| 6,650,369 B2 | 11/2003 | Koizumi et al. |
| 6,682,942 B1 | 1/2004 | Wagner et al. |
| 6,791,613 B2 | 9/2004 | Shinohara et al. |
| 7,030,922 B2 | 4/2006 | Sakuragi |
| 7,110,030 B1 | 9/2006 | Kochi et al. |
| 7,116,365 B1 | 10/2006 | Ueno et al. |
| 7,277,130 B2 | 10/2007 | Korthout et al. |
| 7,283,168 B2 | 10/2007 | Watanabe |
| 7,317,483 B2 | 1/2008 | Tanimoto |
| 7,375,753 B2 | 5/2008 | Mabuchi |
| 7,714,920 B2 | 5/2010 | Inagaki et al. |
| 2002/0110932 A1 | 8/2002 | Wagner et al. |
| 2002/0115225 A1 | 8/2002 | Wagner et al. |
| 2003/0137594 A1 | 7/2003 | Koizumi et al. |
| 2003/0138973 A1 | 7/2003 | Wagner et al. |
| 2004/0027471 A1 | 2/2004 | Koseki et al. |
| 2004/0175300 A1 | 9/2004 | Indermuhle et al. |
| 2004/0197931 A1 | 10/2004 | Indermuhle et al. |
| 2004/0251396 A1 | 12/2004 | Koyama |
| 2005/0083408 A1 | 4/2005 | Mabuchi |
| 2005/0128326 A1 | 6/2005 | Korthout et al. |
| 2005/0281816 A1 | 12/2005 | Lamping et al. |

(Continued)

FOREIGN PATENT DOCUMENTS

| | | |
|---|---|---|
| EP | 0 865 197 A2 | 9/1998 |
| EP | 908957 A2 | 4/1999 |

(Continued)

OTHER PUBLICATIONS

Gooding et al., "Amperometric biosensor with enzyme amplification fabricated using self-assembled monolayers of alkanethiols: the influence of the spatial distribution of the enzymes", Electrochemistry Communications, vol. 2, No. 4, Apr. 1, 2000, pp. 217-221.
International Search Report issued in International Application No. PCT/JP2011/004127 issued on Aug. 16, 2011.
International Search Report mailed Mar. 29, 2011 issued in corresponding International Application No. PCT/JP2011/001185.
International Search Report issued in International Patent Application No. PCT/JP2011/007239 dated Feb. 7, 2012.
International Search Report issued in International Application No. PCT/JP2011/007238 with Date of mailing Feb. 7, 2012.

(Continued)

*Primary Examiner* — Chih-Min Kam
(74) *Attorney, Agent, or Firm* — McDermott Will & Emery LLP

(57) ABSTRACT

Provided are a method for increasing an amount of glucose oxidase to be immobilized on the self-assembled monolayer and a sensor which comprises glucose oxidase immobilized with the method. The method of the disclosed technology is characterized by that one molecule of an amino acid is interposed between the self-assembled monolayer and the molecule of the glucose oxidase.

21 Claims, 3 Drawing Sheets

(56) References Cited

U.S. PATENT DOCUMENTS

| | | |
|---|---|---|
| 2006/0001751 A1 | 1/2006 | Abe et al. |
| 2009/0011952 A1 | 1/2009 | Gau |
| 2009/0042744 A1 | 2/2009 | Wagner et al. |
| 2009/0047685 A1 | 2/2009 | Kohno et al. |
| 2009/0047695 A1 | 2/2009 | Wagner et al. |
| 2009/0202580 A1 | 8/2009 | Uggeri et al. |
| 2009/0325262 A1 | 12/2009 | Hodneland et al. |
| 2010/0113476 A1 | 5/2010 | Chen et al. |
| 2010/0233827 A1 | 9/2010 | Kusaki et al. |
| 2012/0238036 A1 | 9/2012 | Hataoka |
| 2013/0029364 A1 | 1/2013 | Hataoka |

FOREIGN PATENT DOCUMENTS

| | | |
|---|---|---|
| GB | 2 347 212 A | 8/2000 |
| JP | 01-209370 A | 8/1989 |
| JP | 07-113637 B | 12/1995 |
| JP | 9-247537 A | 9/1997 |
| JP | 10-93066 A | 4/1998 |
| JP | 11-014627 A | 1/1999 |
| JP | 11-112018 A | 4/1999 |
| JP | 2000-515965 A | 11/2000 |
| JP | 2001-045375 A | 2/2001 |
| JP | 2001-305139 A | 10/2001 |
| JP | 2002-511215 A | 4/2002 |
| JP | 2002-520618 A | 7/2002 |
| JP | 2002-520618 A | 7/2002 |
| JP | 2002-520621 A | 7/2002 |
| JP | 2002-237584 A | 8/2002 |
| JP | 2003-230055 A | 8/2003 |
| JP | 2005-509737 A | 4/2005 |
| JP | 2006-502719 A | 1/2006 |
| JP | 2006-166837 A | 6/2006 |
| JP | 2006-208012 A | 8/2006 |
| JP | 2006-266707 A | 10/2006 |
| JP | 2006-266707 A | 10/2006 |
| JP | 2007-528850 A | 10/2007 |
| JP | 2007-298334 A | 11/2007 |
| JP | 2009-222401 A | 10/2009 |
| JP | 2009-541259 A | 11/2009 |
| JP | 2010-117140 A | 5/2010 |
| JP | 2010-237191 A | 10/2010 |
| JP | 2010-532475 A | 10/2010 |
| WO | 89/11100 A1 | 11/1989 |
| WO | 98/00714 A1 | 1/1998 |
| WO | 98/56170 A1 | 12/1998 |
| WO | 00/04382 A1 | 1/2000 |
| WO | 00/04390 A2 | 1/2000 |
| WO | WO-00/04382 A1 | 1/2000 |
| WO | 03/018854 A2 | 3/2003 |
| WO | 03/069897 A1 | 8/2003 |
| WO | 2005/018413 A2 | 3/2005 |
| WO | 2007/063616 A1 | 6/2007 |
| WO | 2009/005567 A1 | 1/2009 |
| WO | 2011/089903 A1 | 7/2011 |
| WO | 2012/029202 A1 | 3/2012 |
| WO | 2012/053138 A1 | 4/2012 |
| WO | 2012/168988 A1 | 12/2012 |
| WO | 2013/005269 A1 | 1/2013 |

OTHER PUBLICATIONS

Besselink et al., "N-hydroxysuccinimide-activated glycine-sepharose," Applied Biochemistry and Biotechnology 2003, vol. 43, pp. 227-246.

Diamandis et al., "The biotin-(strept)avidin system: principles and applications in biotechnology," Clin. Chem. 1991, vol. 37, No. 5, pp. 625-636.

Non-Final Office Action issued in U.S. Appl. No. 13/629,121 dated Jan. 4, 2013.

Non-Final Office Action issued in U.S. Appl. No. 13/629,121 dated Mar. 5, 2013.

Non-Final Office Action issued in U.S. Appl. No. 13/629,121 dated Sep. 16, 2013.

International Search Report issued in International Application No. PCT/JP2011/005037 with Date of mailing Oct. 11, 2011, with English Translation.

Kondo et al., "Plasma-Assisted Immobilization of Heparin onto Low-Density Polyethylene Surface," Chem. Pharm. Bull., 2008, vol. 56, No. 7, p. 921-925.

Shriver-Lake et al., Antibody Immobilization Using Heterobifunctional Crosslinkers, Biosensors & Bioelectronics, 1997, vol. 12, No. 11, p. 1101-1106.

Notice of Allowance issued in U.S. Appl. No. 13/483,840 dated Oct. 31, 2013.

Final Office Action issued in U.S. Appl. No. 13/483,840 dated Sep. 13, 2013.

Non-Final Office Action issued in U.S. Appl. No. 13/483,840 dated Feb. 27, 2013.

Non-Final Office Action issued in U.S. Appl. No. 13/483,840 dated Sep. 27, 2012.

International Search Report issued in International Application No. PCT/JP2011/000268 with Date of mailing Apr. 5, 2011.

English translation of Chinese Search Report issued in Chinese Patent Application No. 201180037848.6 issued Mar. 3, 2014.

Related Art

Related Art

METHOD FOR IMMOBILIZING GLUCOSE OXIDASE ON A SELF-ASSEMBLED MONOLAYER

CROSS-REFERENCE TO RELATED APPLICATIONS

This is a continuation of International Application No. PCT/JP2011/004127, with an international filing date of Jul. 21, 2011, which claims priority of Japanese Patent Application No. 2010-234314, filed on Oct. 19, 2010, the contents of which are hereby incorporated by reference.

TECHNICAL FIELD

The disclosure relates to a method for immobilizing glucose oxidase on a self-assembled monolayer.

BACKGROUND

A biosensor is used to detect or quantify a target substance contained in a sample. Some of biosensors comprise glucose oxidase to detect or quantify glucose.

When a sample containing glucose is supplied to the biosensor comprising glucose oxidase, the glucose is decomposed into gluconolactone and hydrogen peroxide by the glucose oxidase. At least one of the gluconolactone and hydrogen peroxide is detected or quantified, to detect or quantify the glucose contained in the sample.

Patent Literature 1 discloses a prior biosensor comprising enzyme. FIG. 2 shows a biosensor disclosed in FIG. 7 of Patent Literature 1.

According to the description regarding FIG. 7 of Patent Literature 1, the biosensor is used for screening of biomoleculer activity. The biosensor comprises a monolayer 7, an affinity tag 8, an adaptor molecule 9, and a protein 10. The monolayer 7 is composed of a self-assembled monolayer represented by chemical formula: X—R—Y (see Page 24 lines 23-26, Page 25 lines 3-20, Page 25 line 27-Page 26 line 13, and Page 26 lines 14-22 of Patent Literature 1). Examples of X, R, and Y are HS—, an alkane, and a carboxyl group, respectively (see Page 25 lines 3-20, Page 25 lines 27-Page 26 line 13, and Page 28 lines 21-23 of Patent Literature 1).

CITATION LIST

Patent Literature

[Patent Literature 1]
WO00/04382, which corresponds to Japanese Unexamined Patent Application Publication (Translation of PCT Application) No. 2002-520618 (see paragraph [0080], [0082], [0084], [0085], [0095], [0109], [0118], and [0119])

SUMMARY OF THE INVENTION

Technical Problem

In order to improve the detection sensitivity or the quantification accuracy of glucose, it is required to increase an amount of glucose oxidase to be immobilized on the biosensor.

The present inventor has discovered that the amount of the immobilized glucose oxidase per unit area was increased significantly by binding one molecule amino acid to a self-assembled monolayer and then immobilizing glucose oxidase. The invention has been provided on the basis of the discovery.

Thus, provided herein are a method for increasing an amount of glucose oxidase to be immobilized on the self-assembled monolayer, and a sensor with the glucose oxidase immobilized in accordance with the same method.

Solution to Problem

The following items (A1) to (C6) solve the above problem(s).

(A1) A method for immobilizing a glucose oxidase on a self-assembled monolayer, comprising the following steps (a) and (b) in this order:

a step (a) of preparing a substrate comprising one molecule of an amino acid and the self-assembled monolayer, wherein the one molecule of the amino acid is bound to the self-assembled monolayer through a peptide bond represented by the following chemical formula (I):

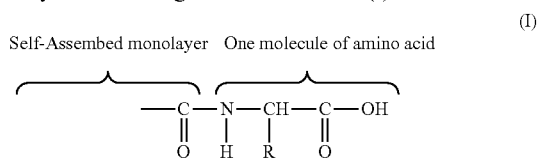

(I)

(wherein R represents side chain of the one molecule of the amino acid)

the one molecule of the amino acid is selected from the twenty kinds of amino acids consisting of cysteine, lysine, histidine, phenylalanine, tyrosine, glycine, asparagine, methionine, serine, tryptophan, leucine, glutamine, alanine, isoleucine, threonine, proline, glutamate, aspartate, arginine, and valine, and a step (b) of supplying the glucose oxidase to the substrate to form a peptide bond represented by the following chemical formula (II) as a result of reaction between the carboxyl group of the one molecule of the amino acid and the amino group of the glucose oxidase

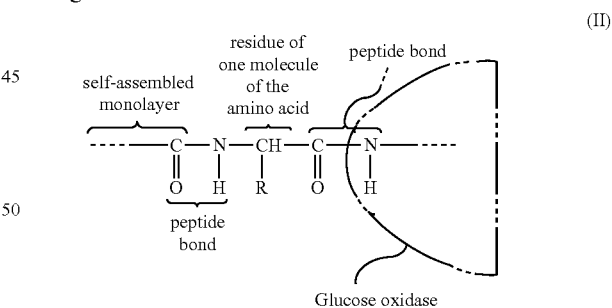

(II)

(wherein R represents side chain of the one molecule of the amino acid).

(A2) The method according to (A1), wherein the step (a) comprises the following steps (a1) and (a2):

a step (a1) of preparing a substrate comprising a self-assembled monolayer on the surface thereof, the self-assembled monolayer having a carboxyl acid at one end, and a step (a2) of supplying the one molecule of the amino acid to form a peptide bond represented by the chemical formula (I) as a result of reaction between the carboxyl group of the one end of the self-assembled monolayer and the amino group of the one molecule of the amino acid.

(A3) The method according to (A1), further comprising the following step (ab) between the step (a) and the step (b):

a step (ab) of activating the carboxyl group of the one molecule of the amino acid with a mixture of N-Hydroxysuccinimide and 1-ethyl-3-(3-dimethylaminopropyl) carbodiimide hydrochloride.

(A4) The method according to claim (A2), further comprising the following step (a1a) between the step (a1) and the step (a2):

a step (a1a) of activating the carboxyl group of the self-assembled monolayer with a mixture of N-Hydroxysuccinimide and 1-ethyl-3-(3-dimethylaminopropyl) carbodiimide hydrochloride.

(A5) The method according to (A1), wherein the chemical formula (II) is represented by the following chemical formula (III).

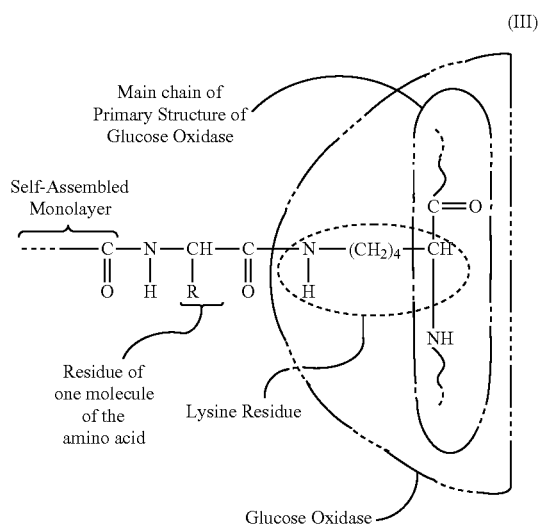

(wherein R represents side chain of the one molecule of the amino acid)

(A6) The method according to (A1), wherein the one molecule of the amino acid is selected from the group consisting of cysteine, lysine, histidine, phenylalanine, glycine, methionine, serine, alanine, asparagine, leucine, tyrosine, glutamate, isoleucine, threonine, aspartate, tryptophan, valine, argnine, and proline.

(A7) The method according to (A1), wherein the one molecule of the amino acid is selected from the group consisting of cysteine, lysine, histidine, phenylalanine, glycine, methionine, serine, alanine, asparagine, leucine, tyrosine, glutamate, isoleucine, threonine, aspartate, tryptophan, and valine.

(A8) The method according to (A1), wherein the one molecule of the amino acid is selected from the group consisting of cysteine, lysine, histidine, phenylalanine, glycine, methionine, serine, alanine, asparagine, leucine.

(A9) The method according to (A1), wherein the one molecule of the amino acid is selected from the group consisting of cysteine, lysine, histidine, phenylalanine, glycine, methionine, serine, and alanine.

(B1) A sensor comprising a self-assembled monolayer, one molecule of an amino acid, and a glucose oxidase, wherein, the one molecule of the amino acid is interposed between the self-assembled monolayer and the glucose oxidase, the glucose oxidase is bound to the self-assembled monolayer through two peptide bonds represented by the following chemical formula (II),

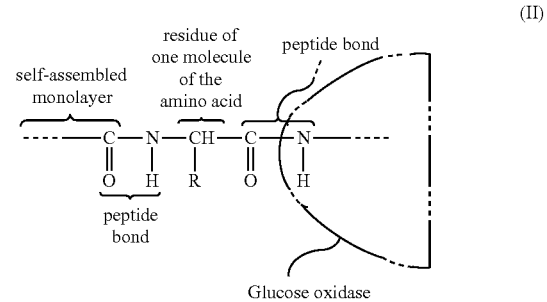

(wherein R represents side chain of the one molecule of the amino acid)

the one molecule of the amino acid is selected from the twenty kinds of amino acids consisting of cysteine, lysine, histidine, phenylalanine, tyrosine, glycine, asparagine, methionine, serine, tryptophan, leucine, glutamine, alanine, isoleucine, threonine, proline, glutamate, aspartate, argnine, and valine.

(B2) The sensor according to (B1), wherein the chemical formula (II) is represented by the following chemical formula (III).

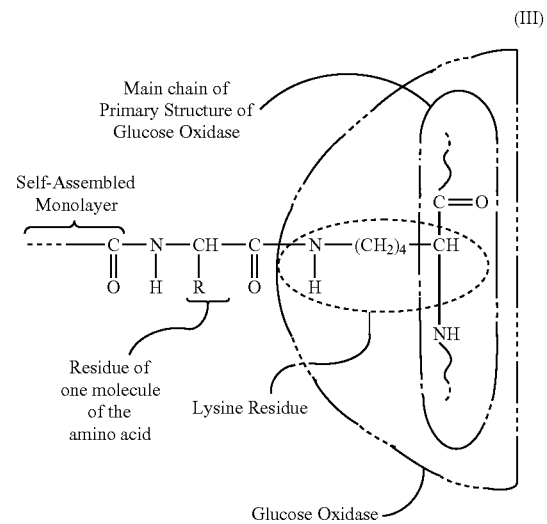

(wherein R represents side chain of the one molecule of the amino acid)

(B3) The sensor according to (B1), wherein the one molecule of the amino acid is selected from the group consisting of cysteine, lysine, histidine, phenylalanine, glycine, methionine, serine, alanine, asparagine, leucine, tyrosine, glutamate, isoleucine, threonine, aspartate, tryptophan, valine, argnine, and proline.

(B4) The sensor according to (B1), wherein the one molecule of the amino acid is selected from the group consisting of cysteine, lysine, histidine, phenylalanine, glycine, methionine, serine, alanine, asparagine, leucine, tyrosine, glutamate, isoleucine, threonine, aspartate, tryptophan, and valine.

(B5) The sensor according to (B1), wherein the one molecule of the amino acid is selected from the group consisting of cysteine, lysine, histidine, phenylalanine, glycine, methionine, serine, alanine, asparagine, leucine.

(B6) The sensor according to (B1), wherein the one molecule of the amino acid is selected from the group consisting of cysteine, lysine, histidine, phenylalanine, glycine, methionine, serine, and alanine.

(C1) A method for detecting or quantifying glucose contained in a sample with a sensor, comprising the following steps (a) to (c) in this order, a step (a) of preparing the sensor comprising a self-assembled monolayer, one molecule of an amino acid, and a glucose oxidase, wherein, the one molecule of the amino acid is interposed between the self-assembled monolayer and the glucose oxidase, the glucose oxidase is bound to the self-assembled monolayer through two peptide bonds represented by the following chemical formula (II),

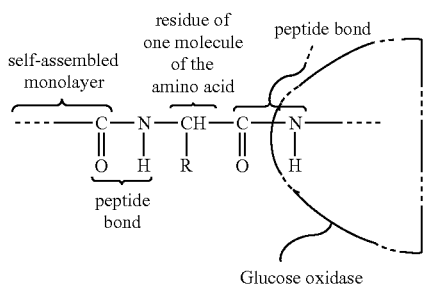

(II)

(wherein R represents side chain of the one molecule of the amino acid)

the one molecule of the amino acid is selected from the twenty kinds of amino acids consisting of cysteine, lysine, histidine, phenylalanine, tyrosine, glycine, asparagine, methionine, serine, tryptophan, leucine, glutamine, alanine, isoleucine, threonine, proline, glutamate, aspartate, argnine, arginine, and valine, a step (b) of supplying the sample to the sensor to generate gluconolactone and hydrogen peroxide due to decomposition of the glucose by the glucose oxidase, a step (c) of detecting or quantifying at least one of the gluconolactone and the hydrogen peroxide to detect or quantify the glucose contained in the sample.

(C2) The method according to (C1), wherein the chemical formula (II) is represented by the following chemical formula (III).

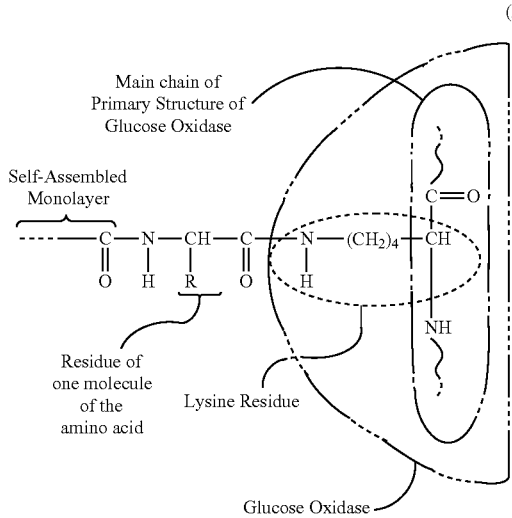

(III)

(wherein R represents side chain of the one molecule of the amino acid)

(C3) The method according to (C1), wherein the one molecule of the amino acid is selected from the group consisting of cysteine, lysine, histidine, phenylalanine, glycine, methionine, serine, alanine, asparagine, leucine, tyrosine, glutamate, isoleucine, threonine, aspartate, tryptophan, valine, argnine, and proline.

(C4) The method according to (C1), wherein the one molecule of the amino acid is selected from the group consisting of cysteine, lysine, histidine, phenylalanine, glycine, methionine, serine, alanine, asparagine, leucine, tyrosine, glutamate, isoleucine, threonine, aspartate, tryptophan, and valine.

(C5) The method according to (C1), wherein the one molecule of the amino acid is selected from the group consisting of cysteine, lysine, histidine, phenylalanine, glycine, methionine, serine, alanine, asparagine, leucine.

(C6) The method according to (C1), wherein the one molecule of the amino acid is selected from the group consisting of cysteine, lysine, histidine, phenylalanine, glycine, methionine, serine, and alanine.

Advantageous Effect of Invention

The exemplary embodiments achieve significant increase of the amount of the glucose oxidase to be immobilized per unit area.

DESCRIPTION OF EMBODIMENT

An exemplary embodiment is described below with reference to FIG. 1.

Embodiment 1

Figure 1:
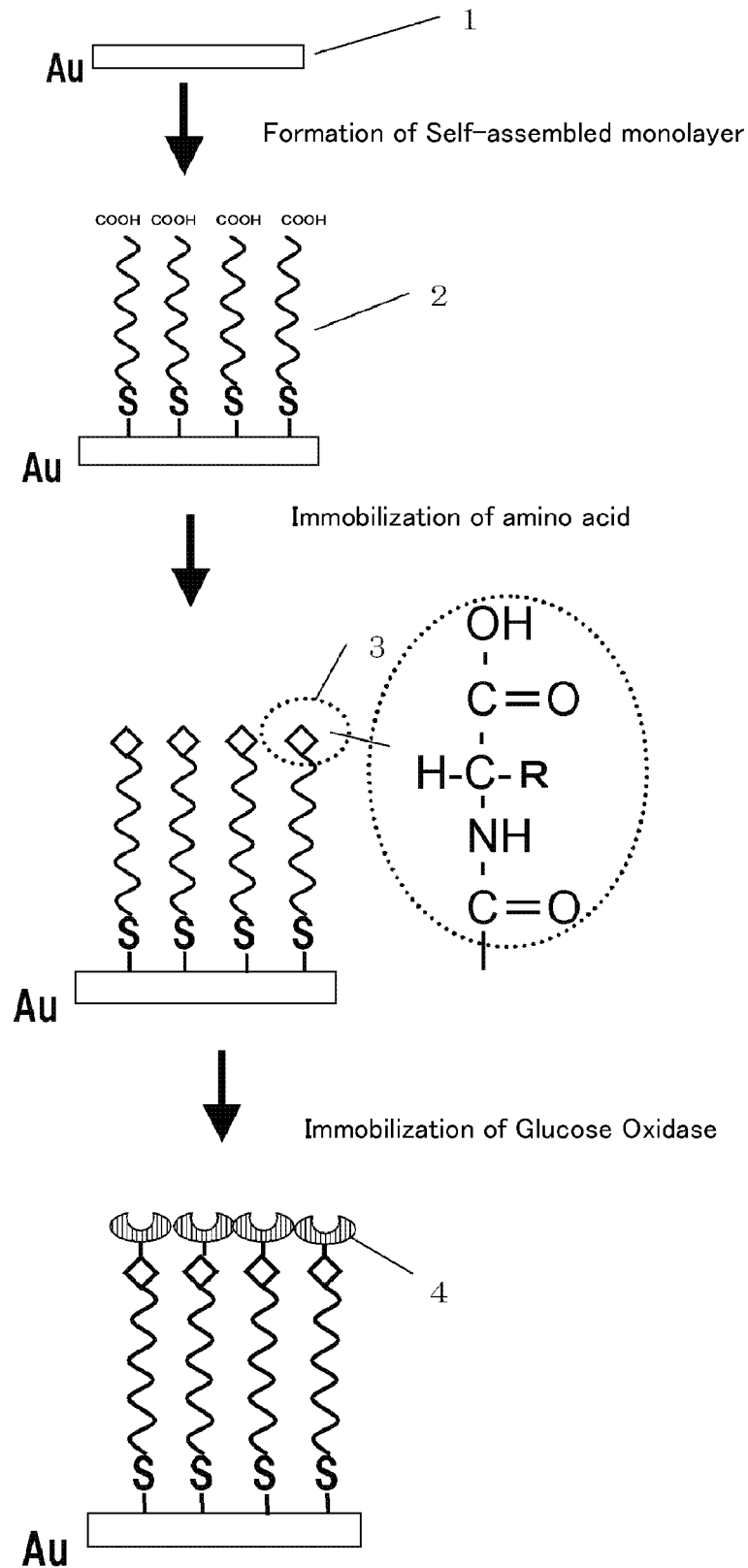
FIG. 1 shows a schematic view of a method according to an exemplary embodiment.
Figure 2:
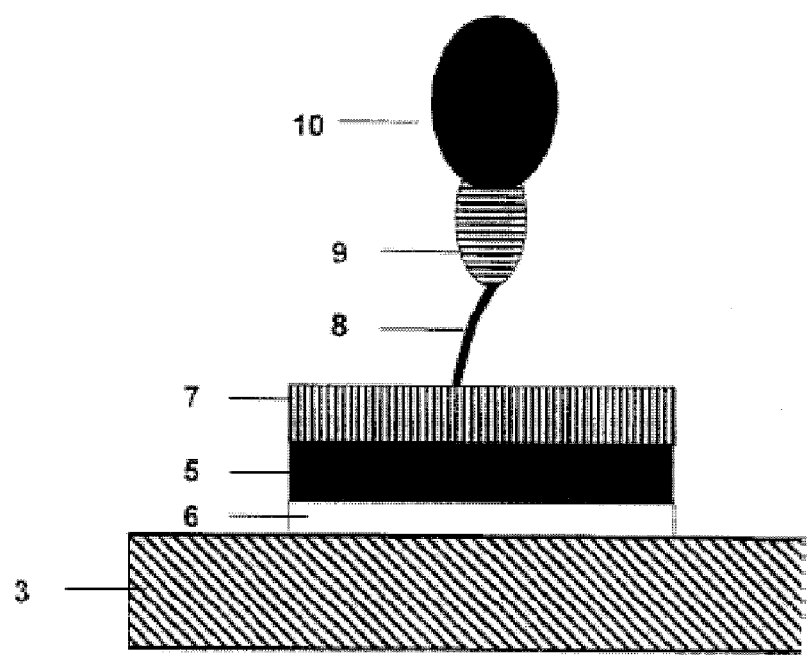
FIG. 2 is FIG. 7 of Patent Literature 1.

FIG. 1 shows a method according to an exemplary embodiment for immobilizing a glucose oxidase on a self-assembled monolayer.

Preferably, a substrate 1 is a gold substrate. An example of the gold substrate is a substrate having gold uniformly on its surface. Specifically, the gold substrate may be a substrate having a gold film formed with a sputtering method on the surface of glass, plastic, or $SiO_2$.

First, the substrate 1 is immersed into a solvent containing an alkanethiol. Preferably, the substrate is washed before immersed. The alkanethiol has a carboxyl group at the end thereof. It is preferable that the alkanethiol has carbon number within the range from six to eighteen. Thus, a self-assembled monolayer 2 is formed on the substrate 1.

The preferred concentration of the alkanethiol is approximately 1 mM to 10 mM. The solvent is not limited as long as it dissolves the alkanethiol. Examples of the preferred solvent are ethanol, dimethyl sulfoxide (hereinafter, referred to as "DMSO"), and dioxane. The preferred immersing period is approximately 12 to 48 hours.

Next, an amino acid 3 is supplied to the self-assembled monolayer 2. The carboxyl group (–COOH), which locates at the top end of the self-assembled monolayer 2, reacts with an amino group (–$NH_2$) of the amino acid 3 to form a peptide bond represented by the following the chemical formula (I).

(I)

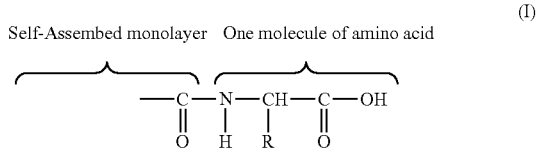

(wherein R represents side chain of the one molecule of the amino acid)

In the chemical formula (I), one molecule of the amino acid 3 binds to the self-assembled monolayer 2.

The amino acid 3 is selected from twenty kinds of amino acids consisting of cysteine, lysine, histidine, phenylalanine, tyrosine, glycine, asparagine, methionine, serine, tryptophan, leucine, glutamine, alanine, isoleucine, threonine, proline, glutamate, aspartate, argnine, and valine. Namely, in the chemical formula (I), R is the side chain of these twenty kinds of amino acids.

When the amino acid 3 is supplied to the self-assembled monolayer 2, two or more kinds of amino acids may be supplied simultaneously. Namely, when a solution containing the amino acid 3 is supplied to the self-assembled monolayer 2, the solution may contain not less than two kinds of the amino acids 3. In light of uniform bind of the glucose oxidase to the amino acid 3, which is described later, it is preferred that the solution contains a sole kind of amino acid.

Subsequently, glucose oxidase 4 is supplied. The 5'-terminal amino group of the glucose oxidase 4 reacts with the carboxyl group of the amino acid 3. The amino group of the lysine contained in the glucose oxidase 4 also reacts with the carboxyl group of the amino acid 3. Thus, two peptide bonds represented by the following chemical formula (II) are formed to obtain a sensor.

(II)

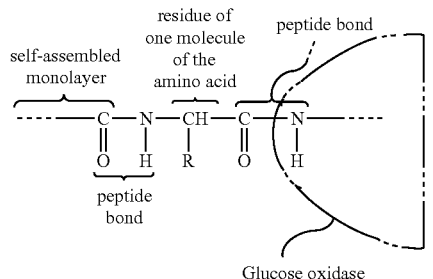

(wherein R represents side chain of the one molecule of the amino acid)

One molecule of the glucose oxidase 4 has only one 5'-terminal, whereas the one molecule of the glucose oxidase 4 has many lysine groups. Therefore, almost all of the chemical formula (II) is represented more specifically by the following chemical formula (III).

(III)

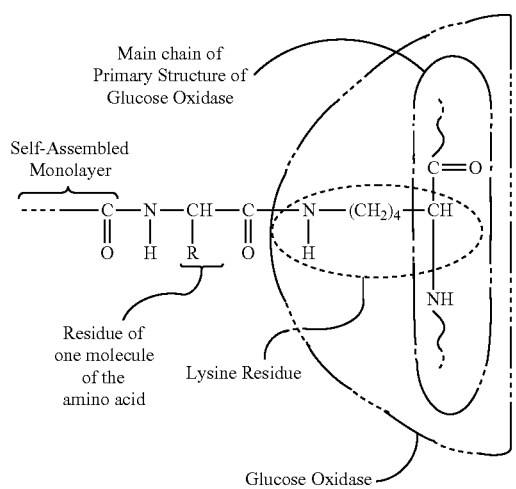

(wherein R represents side chain of the one molecule of the amino acid)

The obtained sensor is used for detecting or quantifying the glucose contained in the sample.

Specifically, glucose is detected or quantified with an electric mediator or peroxidase.

First, the detection or quantification with an electric mediator is described below.

An electric mediator (Oxidant) is added to a sample expected to contain glucose. An example of the electric mediator (Oxidant) is potassium ferricyanide. Subsequently, the sample is supplied to the sensor.

If the sample contains glucose, the glucose oxidase (GOD) converts glucose into gluconic acid, as shown in the following chemical formula (IV). Simultaneously, the electric mediator (Oxidant) is converted into the electric mediator (Reductant). In the chemical formula (IV), potassium ferricyanide is exemplified as the electric mediator (Oxidant).

(IV)

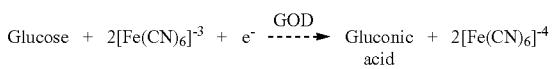

As shown in the following chemical formula (V), the amount of the resultant electric mediator (Reductant) is measured electrochemically to detect or quantify the glucose.

$$[Fe(CN)_6]^{-4} \rightarrow [Fe(CN)_6]^{-3} + e^-$$ (V)

Next, the detection or quantification with peroxidase is described below.

A sample expected to contain glucose is supplied to the sensor in the presence of oxygen and water. If the sample contains glucose, the glucose oxidase (GOD) converts glucose into gluconic acid, as shown in the following chemical formula (VI). Simultaneously, hydrogen peroxide is generated.

(VI)

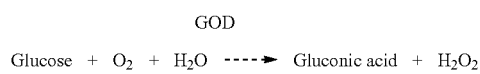

The generated hydrogen peroxide is mixed with a chromogen reagent containing peroxidase. An example of the chromogen is 4-aminoantipyrine, diammonium 2,2'-azinobis [3-ethyl-2,3-dihydrobenzothiazole-6-sulphonate], 3,3',5,5'-tetramethylbenzidine, and 3,3'-diaminobenzidine. After mixing, the chromogen development occurs to detect the glucose. The degree of the chromogen development reveals the concentration of the glucose.

EXAMPLES

The following examples and a comparative example describe the technologies in more detail.

Comparative Example

Figure 3:
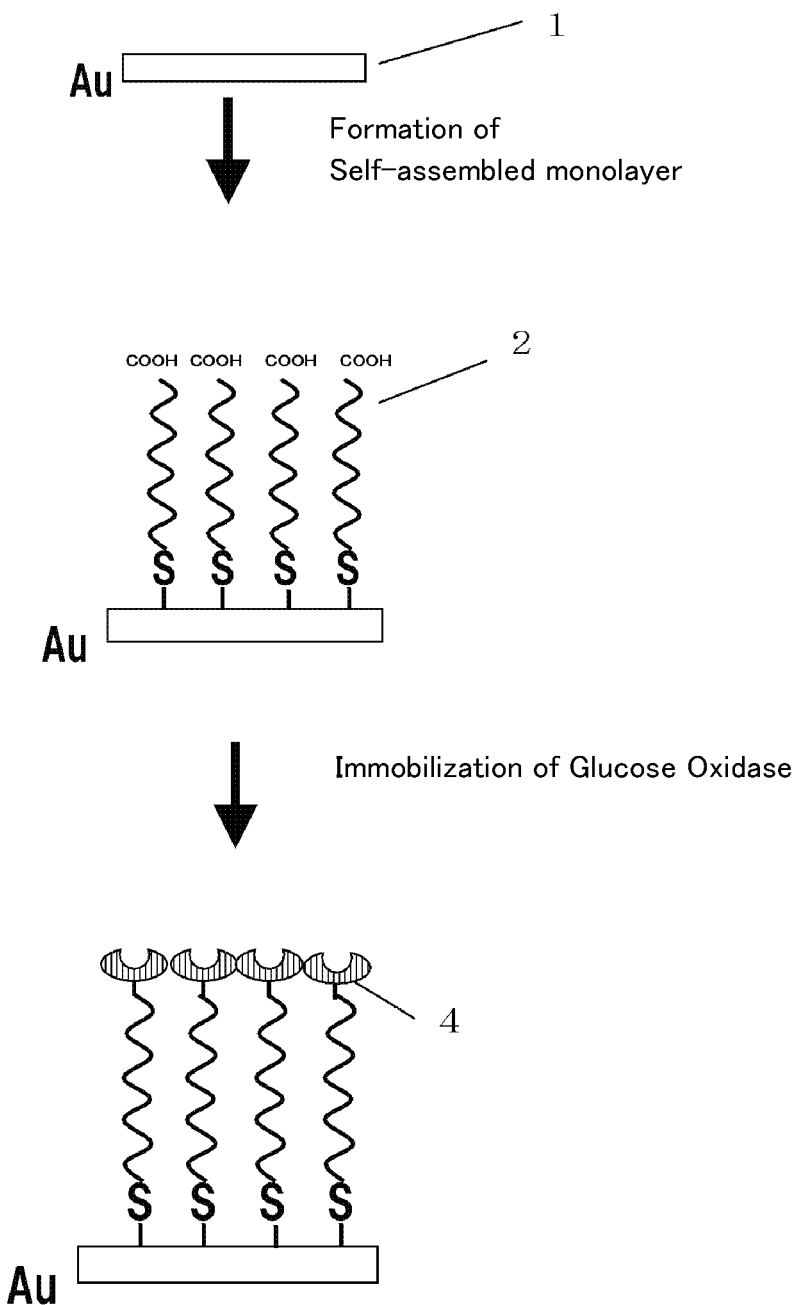
FIG. 3 shows a schematic view of a method according to the related art.

As shown in FIG. 3, glucose oxidase was bound directly with an amide coupling reaction to a carboxyl group located at the top end of self-assembled alkanethiol formed on the gold surface to immobilize the glucose oxidase. The procedure and the results were described below.

[Preparation of a Sample Solution]

A sample solution of 16-Mercaptohexadecanoic acid with final concentration of 10 mM was prepared. The solvent thereof was ethanol.

[Formation of a Self-Assembled Monolayer]

A gold substrate (available from GE healthcare company, BR-1004-05) with gold vapor-deposited on glass was used as a substrate 1. The substrate 1 was washed for ten minutes with a piranha solution containing concentrated sulfuric acid and 30% hydrogen peroxide water. The volume ratio of the concentrated sulfuric acid to the 30% hydrogen peroxide water contained in the piranha solution was 3:1.

Subsequently, the gold substrate was immersed in the sample solution for 18 hours to form a self-assembled monolayer on the surface of the gold substrate. Finally, the substrate 1 was washed with pure water and dried.

[Immobilization of Glucose Oxidase]

Glucose oxidase was bound to the carboxyl acid group located at the top end of the 16-Mercaptohexadecanoic acid which formed the self-assembled monolayer to immobilize the glucose oxidase.

Specifically, the carboxyl acid group located at the top end of the 16-Mercaptohexadecanoic acid was activated with use of 35 microliters of a mixture of 0.1M NHS (N-Hydroxysuccinimide) and 0.4M EDC (1-ethyl-3-(3-dimethylaminopropyl) carbodiimide hydrochloride). Subsequently, thirty-five microliters of glucose oxidase (40 ug/ml) was added at the flow rate of five microliters/minute. Thus, the carboxyl acid of the 16-Mercaptohexadecanoic acid as coupled with the amino group of the glucose oxidase.

Example 1

Experiment was conducted similarly to the comparative example except that glycine was supplied as the one molecule of the amino acid between the formation of the self-assembled monolayer and the immobilization of the glucose oxidase. The procedure and the results are described below.

[Immobilization of Amino Acid (Glycine)]

Glycine was bound with the carboxyl group located at the top end of the 16-Mercaptohexadecanoic acid which formed the self-assembled monolayer 2 to immobilize the glycine.

Specifically, after the carboxyl group was activated similarly to the comparative example, thirty-five microliters of 0.1M glycine (pH: 8.9) was added at the flow rate of 5 microliters/minute. Thus, the carboxyl group of 16-Mercaptohexadecanoic acid was coupled with the amino group of the glycine.

[Immobilization of Glucose Oxidase]

Subsequently, glucose oxidase was bound to the carboxyl group of the glycine to immobilize glucose oxidase. Specifically, after the carboxyl group of the glycine was activated similarly to the above, thirty-five microliters of glucose oxidase (concentration: 250 micrograms/ml) was added at the flow rate of 5 microliters/minute. Thus, the carboxyl group was coupled with the 5'-terminal amino acid of the glucose oxidase or the amino group of the lysine contained in the glucose oxidase.

[Comparison of the Immobilization Amounts]

The immobilization amounts in the example 1 and in the comparative example were measured with use of an SPR device, Biacore 3000 (available from GE healthcare company).

The term "immobilization amount" means the amount of the glucose oxidase immobilized per unit area.

The ratio of the immobilization amount measured in the example 1 to the immobilization amount measured in the comparative example was approximately 30.32:1.

Examples 2 to 20

Threonine, methionine, isoleucine, proline, serine, glutamine, asparagine, phenylalanine, tryptophan, cysteine, histidine, alanine, lysine, leucine, glutamate, valine, aspartate, argnine, and tyrosine were used instead of glycine to measure the respective immobilization amounts similarly to the example 1. These amino acids are twenty kinds of natural amino acid. Table 1 shows the measured immobilization amounts.

TABLE 1

| | | | |
|---|---|---|---|
| Example 11 | Cysteine | 37.69685 | |
| Example 14 | Lysine | 36.59207 | |
| Example 12 | Histidine | 36.16066 | |
| Example 9 | Phenylalanine | 30.35305 | |
| Example 1 | Glycine | 30.32874 | |
| Example 3 | Methionine | 29.62198 | |
| Example 6 | Serine | 29.40409 | |
| Example 13 | Alanine | 26.89383 | |
| Example 8 | Asparagine | 25.171 | |
| Example 15 | Leucine | 23.02633 | |
| Example 20 | Tyrosine | 22.1215 | |
| Example 16 | Glutamate | 20.36339 | |
| Example 4 | Isoleucine | 17.82311 | |
| Example 2 | Threonine | 15.35175 | |
| Example 18 | Aspartate | 14.48565 | |
| Example 10 | Tryptophan | 12.91537 | |
| Example 17 | Valine | 10.40278 | |
| Example 19 | Argnine | 6.055117 | |
| Example 5 | Proline | 5.792629 | |
| Example 7 | Glutamine | 1.202646 | |
| (None) | | 1 | Comparative Example |

A skilled person would understand the following matters from the table 1.

When the twenty kinds of amino acids was used, the immobilization amounts increase, compared to the comparative example. Furthermore, the immobilization amount changes depending on the employed amino acid.

Cysteine, lysine, histidine, phenylalanine, glycine, methionine, serine, alanine, asparagine, leucine, tyrosine, glutamate, isoleucine, threonine, aspartate, tryptophan, valine, argnine, and proline are preferred, because each measured immobilization amounts are five or more in a case where one amino acid selected from these amino acids is supplied.

Cysteine, lysine, histidine, phenylalanine, glycine, methionine, serine, alanine, asparagine, leucine, tyrosine, glutamate, isoleucine, threonine, aspartate, tryptophan, and valine are preferred, because each measured immobilization amounts are ten or more in a case where one amino acid selected from these amino acids is supplied.

Cysteine, lysine, histidine, phenylalanine, glycine, methionine, serine, alanine, asparagine, leucine, and tyrosine are more preferred, because each measured immobilization amounts are the average value (21.6) or more in a case where one amino acid selected from these amino acids is supplied.

Cysteine, lysine, histidine, phenylalanine, glycine, methionine, serine, and alanine, are most preferred, because each measured immobilization amounts are 1.2 times greater than the average value (21.6) in a case where one amino acid selected from these amino acids is supplied.

INDUSTRIAL APPLICABILITY

The technologies achieve significant increase of the amount of the glucose oxidase to be immobilized per unit area. This allows the sensitivity or the accuracy of the biosensor to be improved. The biosensor may be used for an inspection or a diagnosis which requires the detection or the quantification of the glucose contained in the living sample derived from a patient at a clinical practice.

REFERENTIAL SIGNS LIST

1: Gold substrate
2: Alkanethiol
3: Amino Acid
4: Glucose oxidase

The invention claimed is:

1. A method for immobilizing a glucose oxidase on a self-assembled monolayer, comprising the following steps (a) and (b) in this order:

a step (a) of preparing a substrate comprising one molecule of an amino acid and the self-assembled monolayer, wherein the one molecule of the amino acid is bound to the self-assembled monolayer through a peptide bond represented by the following chemical formula (I):

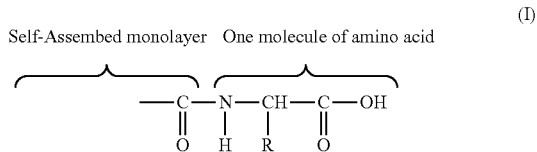

(I)

wherein R represents side chain of the one molecule of the amino acid, the one molecule of the amino acid is selected from the twenty kinds of amino acids consisting of cysteine, lysine, histidine, phenylalanine, tyrosine, glycine, asparagine, methionine, serine, tryptophan, leucine, glutamine, alanine, isoleucine, threonine, proline, glutamate, aspartate, arginine, and valine, and a step (b) of supplying the glucose oxidase to the substrate to form a peptide bond represented by the following chemical formula (II) as a result of reaction between the carboxyl group of the one molecule of the amino acid and the amino group of the glucose oxidase,

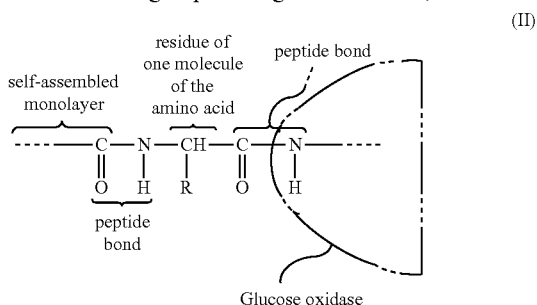

(II)

wherein R represents side chain of the one molecule of the amino acid.

2. The method according to claim 1, wherein the step (a) comprises the following steps (a1) and (a2):

a step (a1) of preparing a substrate comprising a self-assembled monolayer on the surface thereof, the self-assembled monolayer having a carboxyl acid at one end, and a step (a2) of supplying the one molecule of the amino acid to form a peptide bond represented by the chemical formula (I) as a result of reaction between the carboxyl group of the one end of the self-assembled monolayer and the amino group of the one molecule of the amino acid.

3. The method according to claim 2, further comprising the following step (a1a) between the step (a1) and the step (a2):

a step (a1a) of activating the carboxyl group of the self-assembled monolayer with a mixture of N-Hydroxysuccinimide and 1-ethyl-3-(3-dimethylaminopropyl) carbodiimide hydrochloride.

4. The method according to claim 1, further comprising the following step (ab) between the step (a) and the step (b):

a step (ab) of activating the carboxyl group of the one molecule of the amino acid with a mixture of N-Hydroxysuccinimide and 1-ethyl-3-(3-dimethylaminopropyl) carbodiimide hydrochloride.

5. The method according to claim 1, wherein the chemical formula (II) is represented by the following chemical formula (III)

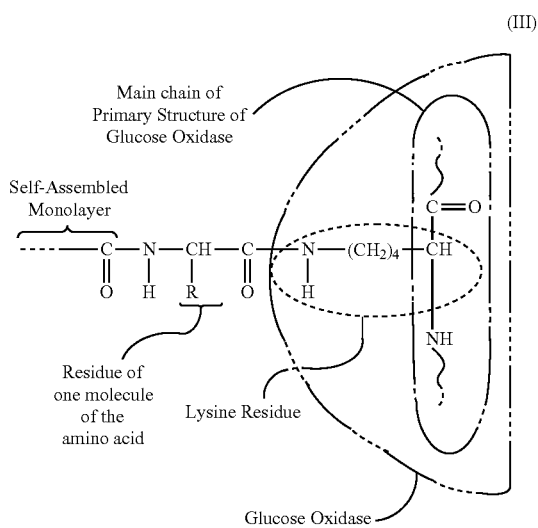

(III)

wherein R represents side chain of the one molecule of the amino acid.

6. The method according to claim 1, wherein the one molecule of the amino acid is selected from the group consisting of cysteine, lysine, histidine, phenylalanine, glycine, methionine, serine, alanine, asparagine, leucine, tyrosine, glutamate, isoleucine, threonine, aspartate, tryptophan, valine, arginine, and proline.

7. The method according to claim 1, wherein the one molecule of the amino acid is selected from the group consisting of cysteine, lysine, histidine, phenylalanine, glycine, methionine, serine, alanine, asparagine, leucine, tyrosine, glutamate, isoleucine, threonine, aspartate, tryptophan, and valine.

8. The method according to claim 1, wherein the one molecule of the amino acid is selected from the group consisting of cysteine, lysine, histidine, phenylalanine, glycine, methionine, serine, alanine, asparagine, and leucine.

9. The method according to claim 1, wherein the one molecule of the amino acid is selected from the group consisting of cysteine, lysine, histidine, phenylalanine, glycine, methionine, serine, and alanine.

10. A sensor comprising a substrate molecule of an amino acid, and a glucose oxidase, wherein, the substrate comprises a self-assembled monolayer and one molecule of an amino acid, the one molecule of the amino acid is interposed between the self-assembled monolayer and the glucose oxidase, the glucose oxidase is bound to the self-assembled monolayer through two peptide bonds represented by the following chemical formula (II),

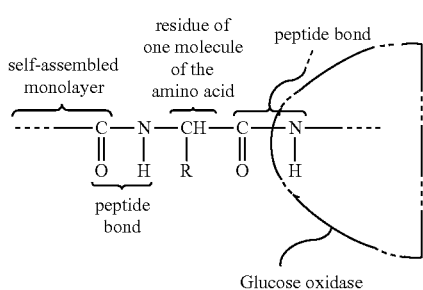

(II)

wherein R represents side chain of the one molecule of the amino acid, the one molecule of the amino acid is selected from the twenty kinds of amino acids consisting of cysteine, lysine, histidine, phenylalanine, tyrosine, glycine, asparagine, methionine, serine, tryptophan, leucine, glutamine, alanine, isoleucine, threonine, proline, glutamate, aspartate, arginine, and valine.

11. The sensor according to claim 10, wherein the chemical formula (II) is represented by the following chemical formula (III)

(III)

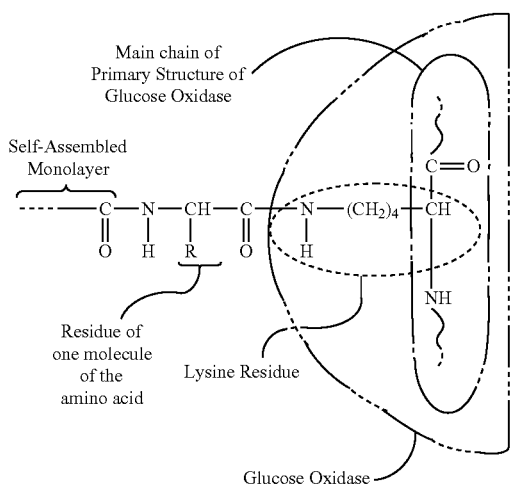

wherein R represents side chain of the one molecule of the amino acid.

12. The sensor according to claim 10, wherein the one molecule of the amino acid is selected from the group consisting of cysteine, lysine, histidine, phenylalanine, glycine, methionine, serine, alanine, asparagine, leucine, tyrosine, glutamate, isoleucine, threonine, aspartate, tryptophan, valine, arginine, and proline.

13. The sensor according to claim 10, wherein the one molecule of the amino acid is selected from the group consisting of cysteine, lysine, histidine, phenylalanine, glycine, methionine, serine, alanine, asparagine, leucine, tyrosine, glutamate, isoleucine, threonine, aspartate, tryptophan, and valine.

14. The sensor according to claim 10, wherein the one molecule of the amino acid is selected from the group consisting of cysteine, lysine, histidine, phenylalanine, glycine, methionine, serine, alanine, asparagine, and leucine.

15. The sensor according to claim 10, wherein the one molecule of the amino acid is selected from the group consisting of cysteine, lysine, histidine, phenylalanine, glycine, methionine, serine, and alanine.

16. A method for detecting or quantifying glucose contained in a sample with a sensor, comprising the following steps (a) to (c) in this order, a step (a) of preparing the sensor comprising a substrate and a glucose oxidase, wherein,
the substrate comprises a self-assembled monolayer and one molecule of an amino acid,
the one molecule of the amino acid is interposed between the self-assembled monolayer and the glucose oxidase,
the glucose oxidase is bound to the self-assembled monolayer through two peptide bonds represented by the following chemical formula (II), (II)

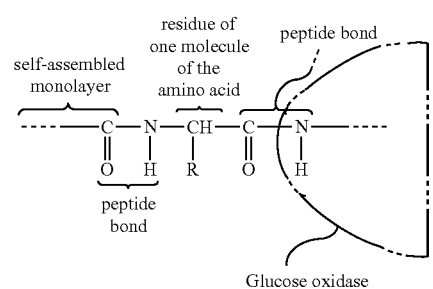

wherein R represents side chain of the one molecule of the amino acid, the one molecule of the amino acid is selected from the twenty kinds of amino acids consisting of cysteine, lysine, histidine, phenylalanine, tyrosine, glycine, asparagine, methionine, serine, tryptophan, leucine, glutamine, alanine, isoleucine, threonine, proline, glutamate, aspartate, arginine, and valine, a step (b) of supplying the sample to the sensor to generate gluconolactone and hydrogen peroxide due to decomposition of the glucose by the glucose oxidase, a step (c) of detecting or quantifying at least one of the gluconolactone and the hydrogen peroxide to detect or quantify the glucose contained in the sample.

17. The method according to claim 16, wherein the chemical formula (II) is represented by the following chemical formula (III)

(III)

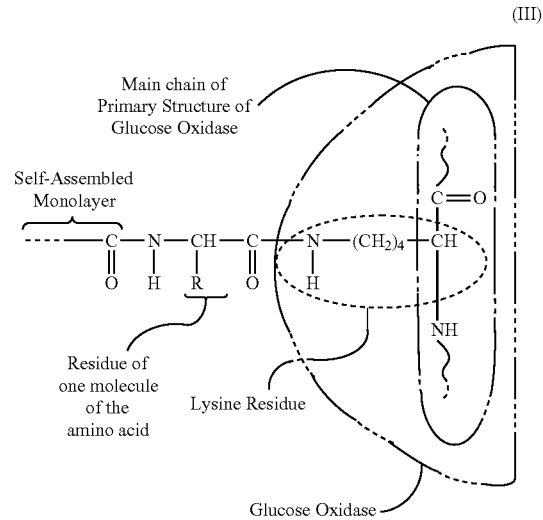

wherein R represents side chain of the one molecule of the amino acid.

18. The method according to claim 16, wherein the one molecule of the amino acid is selected from the group consisting of cysteine, lysine, histidine, phenylalanine, glycine, methionine, serine, alanine, asparagine, leucine, tyrosine, glutamate, isoleucine, threonine, aspartate, tryptophan, valine, arginine, and proline.

19. The method according to claim 16, wherein the one molecule of the amino acid is selected from the group consisting of cysteine, lysine, histidine, phenylalanine, glycine, methionine, serine, alanine, asparagine, leucine, tyrosine, glutamate, isoleucine, threonine, aspartate, tryptophan, and valine.

20. The method according to claim 16, wherein the one molecule of the amino acid is selected from the group consisting of cysteine, lysine, histidine, phenylalanine, glycine, methionine, serine, alanine, asparagine, and leucine.

21. The method according to claim 16, wherein the one molecule of the amino acid is selected from the group consisting of cysteine, lysine, histidine, phenylalanine, glycine, methionine, serine, and alanine.

\* \* \* \* \*